United States Patent [19]

Herrling et al.

[11] Patent Number: 5,321,016

[45] Date of Patent: Jun. 14, 1994

[54] USE OF CERTAIN SUBSTITUTED α-AMINO ACIDS IN TREATING STRESS-RELATED PSYCHIATRIC DISORDERS

[75] Inventors: Paul L. Herrling, Berne; Werner Müller, Gümligen, both of Switzerland

[73] Assignee: Sandoz Pharmaceuticals Corp., E. Hanover, N.J.

[21] Appl. No.: 947,226

[22] Filed: Sep. 18, 1992

Related U.S. Application Data

[60] Division of Ser. No. 747,177, Aug. 19, 1991, Pat. No. 5,162,311, which is a continuation of Ser. No. 499,155, Mar. 26, 1990, abandoned, which is a continuation of Ser. No. 114,881, Oct. 29, 1987, abandoned.

[30] Foreign Application Priority Data

Oct. 30, 1986 [GB] United Kingdom ............... 8625941

[51] Int. Cl.$^5$ .................. A61K 31/66; A61K 31/665
[52] U.S. Cl. .................. 514/114; 514/110; 514/119
[58] Field of Search ............ 514/110, 114, 119

[56] References Cited

U.S. PATENT DOCUMENTS

| | | | |
|---|---|---|---|
| 2,915,547 | 12/1959 | Ratcliffe | 558/190 |
| 3,180,873 | 4/1965 | Schmidt et al. | 548/413 |
| 4,061,697 | 12/1977 | Hübner et al. | 558/190 |
| 4,657,899 | 4/1987 | Rzeszotarski et al. | 514/120 |
| 4,761,405 | 8/1988 | Rzeszotarski et al. | 514/114 |
| 4,918,064 | 4/1990 | Cordi et al. | 514/114 |
| 5,175,153 | 12/1992 | Bigge et al. | 514/114 |

OTHER PUBLICATIONS

*The Merck Manual of Diagnosis and Therapy*; R. Berkow, M.D., ed.; Merck, Sharpe and Dohme Research Laboratories: Rahway, 1977; pp. 1491-1505, 1528-1539, 1553, 1554 and 1551.
Chemical Pharm. Bull., vol. 32, No. 10, pp. 3918-3925 (1984).
Neurol. Neurobiol., pp. 231-234 (1988).
Chem. Abstracts 110: 135709y (1989).

*Primary Examiner*—Mary C. Lee
*Assistant Examiner*—Michael G. Ambrose
*Attorney, Agent, or Firm*—Robert S. Honor; Melvyn M. Kassenoff; Joseph J. Borovian

[57] ABSTRACT

The invention discloses certain substituted α-aminoacids having the formula

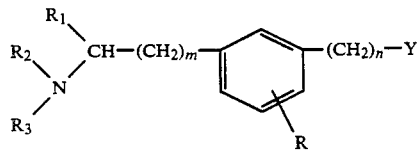

where m and n are 1 or 2, and R, $R_1$, $R_2$, $R_3$ and Y have various significances, which compounds are useful in treating epilepsy, disorders associated with excess GH or LH secretion, anxiety, schizophrenia, depression, CNS degenerative disorders, cerebral hypoxic conditions and stress-related psychiatric disorders.

3 Claims, No Drawings

USE OF CERTAIN SUBSTITUTED α-AMINO ACIDS IN TREATING STRESS-RELATED PSYCHIATRIC DISORDERS

This is a division of application Ser. No. 07/747,177, filed Aug. 19, 1991, now U.S. Pat. No. 5,162,311, which in turn is continuation of application Ser. No. 07/499,155, filed Mar. 26, 1990, which in turn is a continuation of application Ser. No. 07/114,881, filed Oct. 29, 1987, the latter two of which are now abandoned.

The present invention relates to α-amino-α-(3-alkyl-phenyl)alkylethanoic acids, esters or amides, in which the 3-alkyl moiety bears a phosphorus oxo acid group or an ester thereof, wherein phosphorus is attached directly to the alkyl moiety, their salts, processes for their production, pharmaceutical compositions containing them and their use as pharmaceuticals.

It is to be appreciated that the compounds of the invention may be optionally substituted. In particular the phenyl group may be further substituted. Examples of substituents in the phenyl ring are alkoxy, phenyl or phenyl substituted by e.g. halogen, alkyl or phenyl. Furthermore the α-amino group may bear substituents.

In a preferred aspect the present invention relates to compounds of formula I

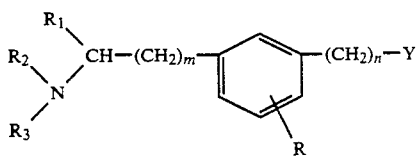

wherein
m and n are independently 1 or 2.
$R_1$ is carboxy, $(C_{1-12})$alkoxycarbonyl, benzoyl$(C_{1-4})$alkoxycarbonyl, phenyl $(C_{2-4})$alkenyloxycarbonyl, carbamoyl, monoalkyl$(C_{1-6})$carbamoyl or dialkyl$(C_{1-6})$carbamoyl,
$R_2$ is hydrogen or $(C_{1-12})$alkyl,
$R_3$ is hydrogen, $(C_{1-12})$alkyl, $(C_{1-18})$alkyl carbonyl, $(C_{2-22})$-alkenylcarbonyl, $(C_{4-22})$alkadienylcarbonyl, $(C_{6-22})$alkatrienylcarbonyl, $(C_{8-22})$alkatetraenylcarbonyl, $(C_{1-12})$alkoxycarbonyl or a group of formula II,

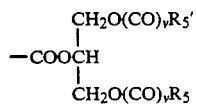

in which $R_5$ and $R_5'$ are each, independently $(C_{1-22})$alkyl, $(C_{2-22})$-alkenyl, $(C_{4-22})$alkadienyl, $(C_{6-22})$alkatrienyl, $(C_{8-22})$alkatetraenyl and v is independently of each other 0 or 1,
R is hydrogen, halogen, hydroxy, $(C_{1-12})$alkyl, $(C_{1-12})$alkoxy, phenyl, phenyl$(C_{1-8})$alkoxy or phenyl$(C_{1-8})$alkyl; phenyl substituted by halogen, $(C_{1-12})$alkyl, $(C_{1-12})$alkoxy, amino, $(C_{1-12})$-alkylcarbonylamino, hydroxy or phenyl and,
Y is one of the groups a), b), c) or d)

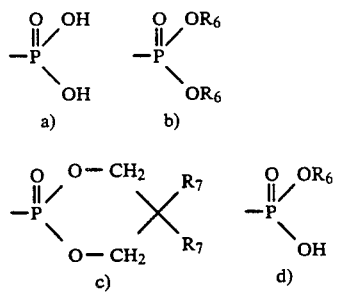

wherein
$R_6$ is $(C_{1-6})$alkyl and
$R_7$ is hydrogen or $(C_{1-6})$alkyl,
or a salt thereof.

Salts of the compounds of the invention are on the one hand metal or ammonium salts of the compounds of the invention having a free carboxy or a free phosphorus oxo acid group, more particularly alkali or alkaline earth metal salts, e.g. sodium, potassium or magnesium salt, and ammonium salts derived from ammonia or organic amines. On the other hand, when a basic nitrogen atom is present the compounds of the invention can form acid addition salts of inorganic or organic acids, e.g. hydrochloric, hydrobromic or maleic acid.

It will be appreciated that the compounds of the invention contain a chiral centre at the carbon atom bearing the α-amino group and can therefore exist in racemic and optically-active forms. It is to be understood that the present invention encompasses the racemic and any optically-active form. Wherein alkenyl groups are present, stereoisomeric forms occur. These isomers are also included within the scope of the present invention.

In one group of compounds of formula I
m and n are independently 1 or 2,
$R_1$ is carboxy or $(C_{1-12})$alkoxycarbonyl,
$R_2$ is hydrogen or $(C_{1-12})$alkyl,
$R_3$ is hydrogen, $(C_{1-12})$alkyl, $(C_{1-12})$alkylcarbonyl, $(C_{2-22})$-alkenylcarbonyl, $(C_{4-22})$alkadienylcarbonyl, $(C_{6-22})$alkatrienylcarbonyl, $(C_{8-22})$alkatetraenylcarbonyl, $(C_{1-12})$alkoxycarbonyl or a group of formula II, in which $R_5$ and $R_5'$ are each, independently $(C_{1-22})$alkyl, $(C_{2-22})$alkenyl, $(C_{4-22})$alkadienyl, $(C_{6-22})$alkatrienyl or $(C_{8-22})$alkatetraenyl and v is independently of each other 0 or 1,
R is hydrogen, halogen, hydroxy, $(C_{1-12})$alkyl, $(C_{1-12})$alkoxy, phenyl, phenyl $(C_{1-8})$alkoxy, phenyl$(C_{1-8})$alkyl or phenyl substituted by halogen $(C_{1-12})$alkyl, $(C_{1-12})$alkoxy or phenyl and,
Y is one of the groups a), b) or c), wherein
$R_6$ is $(C_{1-6})$alkyl and
$R_7$ is hydrogen or $(C_{1-6})$alkyl,
or a salt thereof.

In another group of compounds of formula I, m and n are independently 1 or 2, $R_1$ is carboxy, $(C_{1-12})$alkoxycarbonyl, benzoyl$(C_{1-4})$alkoxycarbonyl, phenyl$(C_{2-4})$alkenyloxycarbonyl or carbamoyl, $R_2$ is hydrogen, $R_3$ is hydrogen or $(C_{1-18})$alkylcarbonyl, R is hydrogen, $(C_{1-12})$alkoxy, phenyl or phenyl substituted by halogen $(C_{1-12})$alkyl, amino or phenyl, and Y is one of the groups a), b), c) or d), wherein $R_6$ is $(C_{1-6})$alkyl and $R_7$ is hydrogen or $(C_{1-6})$alkyl, or a salt thereof.

In the above formula I, the following significances as well as combinations thereof, are preferred:

m is 1.

n is 1.

$R_1$ is carboxy or $(C_{1-4})$alkoxycarbonyl.

$R_2$ is hydrogen.

$R_3$ is hydrogen or $(C_{1-18})$alkylcarbonyl.

R is $(C_{1-12})$alkoxy, phenyl or phenyl substituted by halogen, $(C_{1-4})$alkyl or phenyl.

Y is group a) or group b), wherein $R_6$ is $(C_{1-4})$alkyl or group c), wherein $R_7$ is $(C_{1-4})$alkyl, especially group a).

Halogen is preferably chlorine or fluorine and especially chlorine.

A preferred group of compounds of formula I are compounds of formula Ia

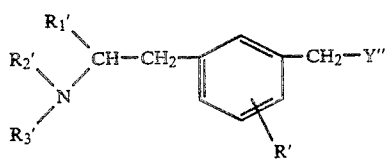

wherein $R_1'$ is carboxy, $(C_{1-4})$alkoxycarbonyl, benzoyl$(C_{1-4})$alkoxycarbonyl, phenyl $(C_{2-4})$alkenyloxycarbonyl or carbamoyl, $R_2'$ is hydrogen, $R_3'$ is hydrogen or $(C_{1-18})$alkylcarbonyl, R' is $(C_{1-12})$-alkoxy, phenyl or phenyl substituted by halogen, $(C_{1-12})$alkyl, amino or phenyl, and Y" is one of the groups a), b) or c), wherein $R_6$ is $(C_{1-6})$alkyl and $R_7$ is hydrogen or $(C_{1-6})$alkyl, or a salt thereof.

The present invention in another aspect provides a process for the production of a compound of the invention which comprises reacting a protected glycine derivative with an appropriate 1-alkyl-3-alkylbenzene, in which one alkyl moiety bears a phosphorus oxo acid ester group wherein phosphorus is attached directly to the alkyl moiety and the other alkyl group bears a leaving group, under basic conditions and hydrolyzing the resulting compound; and, if desired, converting a resulting compound of the invention into another compound of the invention; and/or, if desired, converting a resulting free compound into a salt; and/or, if desired, resolving a racemate obtained into the optical antipodes.

In particular a compound of formula I as defined above can be produced by reacting a compound of formula VI

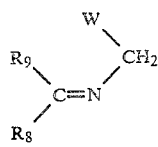

wherein $R_8$ is hydrogen, alkyl or phenyl, $R_9$ is phenyl optionally substituted by chlorine, alkyl or alkoxy, and W is —CN or —COOR$_{10}$, wherein R$_{10}$ is an ester forming radical, with a compound of formula VII,

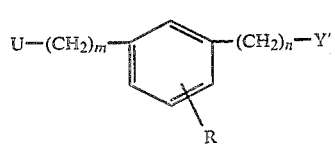

wherein m, n and R are as defined above, U is a leaving group, and Y' is one of the groups b) or c), under basic conditions, and hydrolyzing the resulting compound; and, if desired, converting a resulting compound of formula I into another compound of formula I; and/or, if desired, converting a resulting free compound into a salt; and/or, if desired, resolving a racemate obtained into the optical antipodes.

The process can be effected in conventional manner. Suitable protected glycine derivative are Schiff bases derived from glycine ester or glycinonitrile, in particular a compound of formula VI. $R_{10}$ is e.g. alkyl or phenylalkyl. Preferably $R_8$ and $R_9$ are each phenyl. The reaction of a protected glycine derivative, in particular of a compound of formula VI with a 1-alkyl-3-alkylbenzene, in which one alkyl moiety bears a phosphorus oxo acid ester group wherein phosphorus is attached directly to the alkyl moiety and the other alkyl group bears a leaving group, in particular a compound of formula VII, wherein leaving group U is e.g. halogen, especially bromine, methylsulfonyloxy or p-methylphenylsulfonyloxy, can for example be carried out in a basic two phase system, e.g. a water-immiscible solvent such as dichlormethane and solid or aqueous sodium hydroxide using a phase-transfer catalyst, e.g. benzyltributylammonium chloride. Suitable temperatures range from 0° to room temperature. Alternatively the reaction can also be carried out in an anhydrous organic solvent, such as toluene in the presence of e.g. sodium ethoxide or sodium methoxide at a temperature between 40° and 110° C. The reaction can also be carried out in a water-miscible organic solvent such as dioxane in the presence of an aqueous solution of benzyltrimethylammonium hydroxide at room temperature. The resulting alkylated Schiff base can be hydrolyzed to the corresponding α-amino acid in conventional manner, e.g. with hydrochloric acid. Suitably in compounds of formula VI, W is COOR$_{10}$, wherein R$_{10}$ is alkyl, when compounds of formula I are to be prepared, wherein $R_1$ is esterified carboxy, e.g. alkoxycarbonyl. Using mild reaction conditions for the hydrolysis of the alkylated Schiff base, e.g. dilute hydrochloric acid at room temperature, only the imine functionality is selectively hydrolyzed to yield compounds of formula I, wherein $R_1$ is esterified carboxy and Y is a group b) or c). Concentrated hydrochloric acid at elevated temperature leads to compounds of formula I, wherein $R_1$ is carboxy and Y is group a). Compounds of formula VI, wherein W is CN, are suitably used, when compounds of formula I are to be prepared, wherein $R_1$ is carboxy.

Compounds of formula VI, wherein W is COOR$_{10}$ are conveniently employed when compounds of formula I, wherein $R_1$ is carbamoyl, alkylcarbamoyl or dialkylcarbamoyl, are to be prepared. In this case, the hydrolysis of the alkylated Schiff base is preceded by conversion of the carboxylic acid ester to an amide, e.g. by reaction with ammonia, mono- or dialkylamine to yield compounds of formula I, wherein $R_1$ is carbamoyl, alkylcarbamoyl or dialkylcarbamoyl. Alternatively, compounds of formula I, wherein $R_1$ is carbamoyl, alkylcarbamoyl or dialkylcarbamoyl, may be prepared by reacting a compound of formula I, wherein $R_1$ is esterified carboxy, with ammonia, mono-or dialkylamine.

The compounds of the invention may be converted to other compounds of the invention in conventional manner, e.g. by introducing substituents into the α-amino group, by converting esters to the corresponding acids or acids to esters.

The introduction of substituents into the amino group can be effected in conventional manner. For example the alkylation of the amino group may be carried out with alkyl halides or alkyl sulfates. If only one alkyl group has to be introduced suitably dialkylation is prevented by application of known methods, e.g. N-acylation, alkylation via N-acyl anion, removal of the acyl group. When the compound to be alkylated contains a free carboxy group, (i.e. $R_1$ is carboxy) it is preferably blocked by a protecting group e.g. benzyl removable by selective hydrogenolysis. The acylation of the amino group can be effected by reaction with the appropriate acid or a reactive derivative thereof. The urethane can be prepared by reaction with a haloformic acid ester.

The conversion of an ester to the corresponding acid can be effected by any conventional method, e.g. by hydrolysis. Using selective methods compounds of the invention can be prepared wherein either the phosphonic acid diester or the carboxylic acid ester is converted into the corresponding acid.

For example, compounds of formula I wherein $R_1$ is esterified carboxy and Y is group b) or c) can be converted to compounds of formula I, wherein $R_1$ is esterified carboxy and Y is group a) by silylation with e.g. bromotrimethylsilane and subsequent hydrolysis under mild conditions of the resulting bis-silyl phosphonate. By hydrolyzing compounds of formula I wherein $R_1$ is esterified carboxy and Y is group b) or c) under mild conditions, e.g. dilute hydrochloric acid at elevated temperatures e.g. 60°70° C., compounds of formula I are obtained, wherein $R_1$ is carboxy and Y is a group b) or c).

The esterification can be carried out using conventional methods. When a phosphonic acid monoester [Y is a group d)] is desired the esterification can for example be effected with an alcohol in pyridine in the presence of trichloroacetonitrile at a temperature of about 100° C. When in the starting material to be esterified the amino group is unsubstituted or monosubstituted with a group that is other than a carbonyl-containing group, such amino group is suitably protected by an amino-protecting group. Conventional amino-protecting groups such as benzyloxycarbonyl or tert.-butyloxycarbonyl can be used. The deprotection can be carried out using conventional procedures, e.g. by treatment with trifluoroacetic acid. The benzyloxycarbonyl group can also be removed by hydrogenolysis.

The conversion of a carboxylic acid to an ester can be carried out using conventional methods.

The optional formation of a salt, when the resulting compound of formula I contains a salifiable group may be carried out conventionally.

Racemates can be resolved into the optical antipodes by conventional methods, for example by e.g. separation of diastereoisomeric salts formed by a basic end product with an optically active acid, e.g. by fractional crystallization of d- or l-tartrates, d- or l-di-0,0'-toluyltartrates or d- or l-camphorsulfonates.

Compounds of formula VI used as starting material can be prepared by e.g. condensing a compound of formula VIII, $$H_2N-CH_2-W \qquad VIII$$

wherein W is as defined above, with a compound of formula IX,

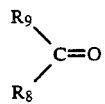

wherein $R_8$ and $R_9$ are as defined above.

The reaction can be effected in known manner.

Compounds of formula VII can be prepared by reacting a compound of formula X

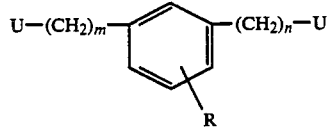

wherein m, n, R and U are as defined above, with a compound of formula XI or XII $$P(OR_6)_3 \qquad XI$$

or

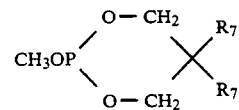

wherein $R_6$ and $R_7$ are as defined above.

The reaction can be carried out in conventional manner.

Insofar as the production of the starting materials for the above processes is not particularly described, these may be produced in analogous manner to known compounds or to processes described herein.

In the following Examples all temperatures are given in degrees centigrade and are uncorrected. The $[\alpha]_D^{20}$- and $[\alpha]_{365}^{20}$- values are also uncorrected.

EXAMPLE 1

($\pm$)-$\alpha$-Amino-3-(4'-chloro-5-phosphonomethyl-[1.1'-biphenyl]-3-yl)propanoic acid To a stirred mixture of 3.7 g of the ketimine of glycinonitrile and benzophenone, 350 mg benzyltributylammonium chloride, 1.6 g sodium hydroxide, 3.2 ml water and 32 ml toluene is added dropwise at 0° over 90 minutes 4.9 g diethyl[3-bromomethyl-5-(4'-chlorophenyl)-phenyl]methylphosphonate. Stirring is then continued at room temperature for 24 hours. Thereafter the reaction mixture is diluted with water and extracted with methylene chloride. The organic layers are washed with water, dried over anhydrous sodium sulfate and evaporated. The residue is chromatographed on 200 g of silica gel (230–400 mesh) with $CH_2Cl_2$/acetic acid ethyl ester (3:1). The fractions with the main product are evaporated in vacuo. The residue is refluxed with 30 ml 7N hydrochloric acid for 12 hours. The mixture is extracted with toluene/ether (1:1). The aqueous layers are evaporated in vacuo, the residue dissolved in tetrahydrofuran/water, treated with propylene oxide and evaporated under vacuum. The residue is stirred in warm methanol to afford the title compound, m.p. 282–285° (decomp.).

The starting material diethyl[3-bromomethyl-5-(4'-chlorophenyl)-phenyl]methylphosphonate may be obtained as follows:

A mixture of 5.9 g 3,5-bis-bromomethyl-[4'-chloro-1.1'-biphenyl], 3.3 ml triethyl phosphite and 60 ml xylene is stirred under reflux for 90 minutes. The mixture is evaporated. The residue is chromatographed on 120 g of silica gel (230–400 mesh) with acetic acid ethyl ester. The fractions with the product are evaporated in vacuo to give the heading compound as a yellow oil.

EXAMPLE 2

(±)-α-Amino-3-(3-phosphonomethyl)phenylpropanoic acid

In manner analogous to that described in Example 1 the title compound, m.p. 271°–275° (decomp.), is obtained.

EXAMPLE 3

(±)-α-Amino-3-(5-phosphonomethyl-[1.1'-biphenyl]-3-yl) propanoic acid

To a stirred mixture of 3.7 g of the ketimine of glycinonitrile and benzophenone, 350 mg benzyltributylammonium chloride, 1.6 g sodium hydroxide, 3.2 ml water and 32 ml toluene is added dropwise at 0° over 90 minutes 4.5 g diethyl[(3-bromomethyl-5-phenyl)phenyl]-methylphosphonate. Stirring is then continued at room temperature for 24 hours. Thereafter the reaction mixture is diluted with water and extracted with methylene chloride. The organic layers are washed with water, dried over anhydrous sodium sulfate and evaporated. The residue is chromatographed on 500 g of silica gel (230–400 mesh ) with acetic acid ethyl ester. The fractions with the main product are evaporated in vacuo. The residue is refluxed with 30 ml 7N hydrochloric acid for 12 hours. The mixture is extracted with toluene/ether (1:1). The aqueous layers are evaporated under vacuum, the residue dissolved in tetrahydrofuran/water, treated with propylene oxide and evaporated under vacuum. The residue is stirred in warm methanol to afford the title compound, m.p. 260°–263° (decomp.).

The starting material diethyl [(3-bromomethyl-5-phenyl)phenyl] methylphosphonate may be obtained as follows:

A mixture of 11.2 g 3,5-bis-bromomethyl-[1.1'-biphenyl], 6.5 ml triethyl phosphite and 110 ml xylene is stirred under reflux for 90 minutes. The mixture is evaporated. The residue is chromatographed on 400 g of silica gel (230–400 mesh) with acetic acid ethyl ester. The fractions with the product are evaporated in vacuo to give the heading compound as a yellow oil.

EXAMPLE 4

(±)-α-Amino-3-(5-octyloxy-3-phosphonomethyl)phenylpropanoic acid

In manner analogous to that described in Example 1 but using (3-bromomethyl-5-octyloxyphenyl)-methylphosphonic acid diethylester as starting material the title compound is prepared, m.p. 243°–246° (decomp.).

EXAMPLE 5

(±)-α-Amino-3-(5-diethoxyphosphinyl)methyl-[1.1'-biphenyl]-3-yl)propanoic acid ethyl ester To a stirred mixture of 5.0 g of the ketimine of glycine ethyl ester and benzophenone, 6.7 g diethyl[(3-bromomethyl-5-phenyl)phenyl]-methylphosphonate, 0.3 g KI and 150 ml dioxane are added dropwise at 10° 7.1 ml aqueous benzyltrimethylammonium hydroxide (40%) over 30 minutes. Stirring is then continued at room temperature for 2 hours. Thereafter the reaction mixture is diluted with water and extracted with toluene. The organic layer is washed with water, dried ($Na_2SO_4$) and evaporated. The residue is stirred at room temperature with 50 ml 1N HCl and 50 ml ether for 2 hours. The aqueous layer is separated, made alkaline with $NaHCO_3$ and extracted with $CH_2Cl_2$. The organic layer is dried ($Na_2SO_4$) and evaporated to yield the title compound as a yellow oil. M.p. of the hydrochloride 140°–142°, crystallized from ethanol/diethyl ether.

EXAMPLE 6

(±)-α-Amino-3-(5-phosphonomethyl-[1.1'-biphenyl]-3-yl) propanoic acid ethyl ester 5.5 g of the oily base of Example 5 are dissolved in 100 ml abs. $CH_2CL_2$ and treated with 16.5 ml bromotrimethylsilane. The mixture is left at room temperature for 24 hours. After evaporating to dryness the residue is dissolved in 150 ml $H_2O$/ tetrahydrofuran (1:1) and treated with propylene oxide, whereby the title compound crystallizes, m.p. 290°–293° (decomp.).

EXAMPLE 7

(±)-α-Amino-3-(4'-chloro-5-(diethoxyphosphinyl) methyl[1.1'-biphenyl]-3-yl)propanoic acid amide To a stirred mixture of 5.0 g of the ketimine of glycine methyl ester and benzophenone, 8.0 g diethyl [3-bromomethyl-5-(4'-chlorophenyl)phenyl]methylphosphonate, 0.3 g KI and 150 ml dioxane are added dropwise at 10° 7.8 ml aqueous benzyltrimethylammonium hydroxide (40%) over 30 minutes. Stirring is then continued at room temperature for 2 hours. Thereafter the reaction mixture is diluted with water and extracted with toluene. The organic layer is washed with water, dried ($Na_2SO_4$) and evaporated. The residue is taken up in 250 ml $CH_3OH$ and gaseous $NH_3$ is introduced at 10°. The mixture is stirred at room temperature for 66 hours and evaporated. The residue is stirred at room temperature with 70 ml 1N HCl and 70 ml tetrahydrofuran for 1½ hours. The tetrahydrofuran is evaporated and the residue extracted with toluene/diethyl ether (1:1). The aqueous layer is separated, made alkaline with $Na_2CO_3$ and extracted with $CH_2Cl_2$. The organic layer is dried ($Na_2SO_4$) and evaporated to yield the title compound as a foam.

$^1$H-NMR (360 MHz,$CDCl_3$): δ 1.25(t,J=6,6H), 1.6 (br.s,2H), 2.9(m,1H), 3.1(m,1H), 3.2(d,J=24,2H), 3.7(m,1H), 4.0(m,4H), 6.6(br. s,2H), 7.1–7.6(7H).

EXAMPLE 8

(±)-α-Amino-3-(4'-chloro-5-phosphonomethyl-[1.1'-biphenyl]3-yl) propanoic acid amide 4.2 g of the Example 7 compound are dissolved in 50 ml $CH_2CL_2$ and treated with 17.7 ml bromotrimethylsilane. The mixture is stirred for 48 hours. After evaporation the residue is taken up with $CH_3OH$ and evaporated. This procedure is effected 3 times. The residue is crystallized from $CH_3OH$/ethyl acetate (1:1), to yield the title compound, m.p. 278°–280° (decomp.).

EXAMPLE 9

(±)-α-Palmitoylamino-3-(5-phosphonomethyl-[1.1'-biphenyl]3-yl) propanoic acid

To a mixture of 335 mg (±)-α-amino-3-(5-phosphonomethyl-[1.1'-biphenyl]3-yl) propanoic acid in 30 ml dimethyl formamide and 0.76 ml N-ethyldiisopropylamine under nitrogen are added dropwise at room temperature within 10 minutes 0.4 ml palmitic acid chloride. The mixture is stirred at room temperature for 26 hours. The solvent is evaporated in vacuo. The oily residue is taken up in water, acidified with 2N HCl to pH 1 and extracted with diethyl ether. The extract is washed with saturated aqueous sodium chloride solution, dried ($Na_2SO_4$) and evaporated. The residue is recrystallized from diethyl ether/petroleum ether to yield the title compound, m.p. 130°–140°. MS (FAB):574(MH+).

EXAMPLE 10

(±)-α-Amino-3-(4'-chloro-5-(diethoxyphosphinyl)-methyl-[1.1'-biphenyl]-3-yl)-propanoic acid methyl ester In analogous manner to that described in Example 5 using the ketimine of glycine methyl ester and benzophenone and diethyl[3-bromomethyl-5-(4'-chlorophenyl)phenyl]methylphosphonate, the title compound is obtained as an oil, DC in $CH_2Cl_2/CH_3OH$ (9:1) Rf=0.46.

EXAMPLE 11

(±)-α-Amino-3-(4'-chloro-5-phosphonomethyl-[1.1'-biphenyl]-3-yl) propanoic acid methyl ester In manner analogous to that described in Example 6 the title compound is obtained, m.p. 300°–305° (decomp.).

EXAMPLE 12

(±)-α-Amino-3-(4'-chloro-5-phosphonomethyl-[1.1'-biphenyl]-3-yl) propanoic acid cinnamyl ester a) (±)-α-Amino-3-(4'-chloro-5-(diethoxyphosphinyl)-methyl-[1.1'-biphenyl]-3-yl) propanoic acid 4.6 g (±)-α-amino-3-(4'-chloro-5-(diethoxyphosphinyl)methyl-[1.1'-bi-phenyl] -3-yl)propanoic acid ethyl ester, 1 equivalent of 1N sodium hydroxide and 4 parts by volume of tetrahydrofuran are stirred at room temperature for about 15 hours. The tetrahydrofuran is evaporated in vacuo. The residue is extracted with toluene/diethyl ether (1:1). The pH of the aqueous layer is adjusted to 5, whereby the heading compound crystallizes, m.p. 195°–205° (decomp.).

b) (±)-α-tert.Butyloxycarbonylamino-3-(4'-chloro-5-(diethoxyphosphinyl)methyl-[1.1'-biphenyl]-3-yl) propanoic acid To 1.28 g of the step a) product and 2.2 ml tert.butyl alcohol are added under stirring 3.3 ml 1N aqueous NaOH solution. The mixture is stirred until a clear solution ensues and is then treated dropwise with 0.65 g di-tert.butyl carbonate. The mixture is stirred at room temperature 21 hours. The mixture is then cooled in an ice bath and treated dropwise with a solution of 0.45 g $KHSO_4$ in 3 ml water and extracted 3 times with $CH_2Cl_2$. The combined extracts are evaporated to dryness to give the heading compound, as a white foam, which recrystallized from diethyl ether has a m.p. 110°–114°.

c) (±)-α-tert.Butyloxycarbonylamino-3-(4'-chloro-5-(diethoxyphosphinyl)methyl-[1.1'-biphenyl]-3-yl) propanoic acid cinnamyl ester To a solution of 1.05 g of the product of step b) in 5 ml dimethylformamide are added 362 mg tetramethyl ammonium hydroxide pentahydrate. The mixture is stirred at room temperature 1½ hours and then treated with 394 mg cinnamyl bromide. The mixture is stirred at room temperature 17 hours. The mixture is diluted with ice/water (about 50 ml) and extracted with diethyl ether. The extracts are washed with 10 ml aqueous 1N $KHCO_3$ solution, dried ($Na_2SO_4$) and evaporated to give the heading compound as an oil.

d) (±)-α-Amino-3-(4'-chloro-5-(diethoxyphosphinyl)-methyl-[1.1'-biphenyl]-3-yl)propanoic acid cinnamyl ester 5.5 g of the product of step c) and 50 ml aqueous trifluoroacetic acid (70%) are stirred at room temperature 20 hours. To the mixture are added $CH_2CL_2$ and dropwise aqueous $KHCO_3$ solution. The organic phase is dried ($Na_2SO_4$) and evaporated. The residue is taken up in diethyl ether, filtered and evaporated to dryness, to give the heading compound as an oil.

$^1$H-NMR (80 MHz, $CDCl_3$)δ1.3 (m,6H), 1.8 (br.s,2H), 2.9(m,1H), 3.1 (m,1H), 3.1 (d,J=22,2H), 3.8 (m,1H), 4.0 (m,4H), 4.8 (d,J=6, 2H), 6.3 (m,1H), 6.7 (d,J=15, 1H), 7.0–7.6 (sh,12H).

e) (±)-α-Amino-3-(4'-chloro-5-phosphonomethyl-[1.1'-biphenyl]-3-yl) propanoic acid cinnamyl ester In manner analogous to that described in Example 6 the title compound is obtained, m.p. 253°–255°.

EXAMPLE 13

In manner analogous the following compounds (racemates) are obtained:

| Ex. | $R_1$ | $R_2$ | $R_3$ | R | Y | m.p. | analogous to Ex. |
|---|---|---|---|---|---|---|---|
| a) | $COOC_2H_5$ | H | H | phenyl | 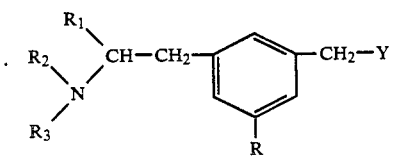 | amorphous[1)] | 5 |

-continued $$R_2\text{-}N(R_3)\text{-}C(R_1)H\text{-}CH_2\text{-}[\text{phenyl}(R)]\text{-}CH_2\text{-}Y$$

| Ex. | $R_1$ | $R_2$ | $R_3$ | R | Y | m.p. | analogous to Ex. |
|---|---|---|---|---|---|---|---|
| b) | COOH | H | H | -C₆H₄-C(CH₃)₃ | -P(O)(OH)₂ | decomp. >330° | 1 |
| c) | COOH | H | H | -C₆H₄-C₆H₅ | -P(O)(OH)₂ | decomp. >295° | 1 |
| d) | COOCH₂CO-C₆H₅ | H | H | -C₆H₄-Cl | -P(O)(OH)₂ | 220–225° (decomp.) | 9 |
| e) | COCCH₃ | H | H | -C₆H₅ | -P(O)(OH)₂ | hydrobromide amorphous[2] | 6 |
| f) | COOH | H | COCH₃ | -C₆H₅ | -P(O)(OH)₂ | amorphous[3] | 8 |
| g) | COOH | H | H | -C₆H₄-NH₂ | -P(O)(OH)₂ | >315°[4] | 1 |

[1] Rf 0.35 (CH₂Cl₂/CH₃OH/conc. NH₃ 9:1:0.1)
[2] ¹H-NMR (360 MHz, DMSO-d₆): δ 3.05(d, J=20, 2H), 3.15(2H), 3.75(s, 3H), 4.45(br.s, 1H), 7.1(s, 1H), 7.65–7.35(7H), 8.45(br.s, 3H)
[3] Rf 0.75 (ethyl acetate/acetic acid/water 5:2:2) ¹H-NMR (60 MHz, CD₃OD): δ i.a. 1.8(s, 3H), 2.9(d, J=22, 2H)
[4] ¹H-NMR (360 MHz, DMSO-d₆): δ i.a. 2.95(d, J=20, 2H), 3.1(m, 2H), 4.1(m, 1H).

EXAMPLE 14

(±)-α-Amino-3-(5-(diethoxyphosphinyl)methyl-[1.1'-biphenyl]-3-yl)propanoic acid ethyl ester An ethereal solution of 29.9 g (±)-α-amino-3-(5-(diethoxyphosphinyl)-methyl-[1.1'-biphenyl]-3-yl)propanoic acid ethyl ester and an ethereal solution of 27.6 g (+)-di-O,O'-p-toluyl-D-tartaric acid are mixed whereby the crude salts precipitate. The salts are filtered and crystallized from ethanol/t-butyl methyl ether (1:4). The resulting crystals are recrystallized three times from isopropanol/tert. butyl methyl ether (1:8) to give pure (+)-α-amino-3-(5-(diethoxyphosphinyl)methyl-[1.1'-biphenyl]-3-yl)propanoic acid ethyl ester (+)-di-O,O'-p-toluyl-D-tartrate, m.p. 155°–158°, $[\alpha]_D^{20} = +88.6°$ (c: 1 in C₂H₅OH/1N HCl 2:1).

The above salt is treated with saturated aqueous KHCO₃ solution and extracted with CH₂CL₂ to give (+)-α-amino-3-(5-(diethoxyphosphinyl) methyl-[1.1'-biphenyl]-3-yl) propanoic acid ethyl ester as an oil. The hydrochloride has a m.p. of 150°–152° (decomp.), crystallized from ethanol/diethyl ether, $[\alpha]_D^{20} = +17.7°$ (c=1 in 2N HCl).

EXAMPLE 15

(+)-α-Amino-3-(5-phosphonomethyl-[1.1'-biphenyl]-3-yl)-propanoic acid ethyl ester In manner analogous to that described in Example 6 and using the compound of Example 14 as starting material, the title compound is obtained m.p. 280°–285° (decomp.), $[\alpha]_D^{20} = +5.0°$ (c=1 in 1N HCl), $[\alpha]_{365}^{20} = +31.0°$ (c=1 in 1N HCl).

EXAMPLE 16

(+)-α-Amino-3-(5-phosphonomethyl-[1.1'-biphenyl]-3-yl) propanoic acid

The compound of Example 15 and 1N hydrochloric acid are heated at 60° for 2 hours. After evaporating to dryness the residue is dissolved in tetrahydrofuran/water and treated with propylene oxide, whereby the title compound is obtained, m.p. 275°–278° (decomp.). $[\alpha]_D^{20} = 0.0 \pm 0.5°$ (c=1 in 6N HCl), $[\alpha]_{365}^{20} = +21.3°$ (c=1 in 6N HCl).

EXAMPLE 17

(−)-α-Amino-3-(5-(diethoxyphosphinyl)methyl-[1.1′-biphenyl]-3-yl)propanoic acid ethyl ester In manner analogous to that described in Example 14 and using (±)-α-amino-3-(5-(diethoxyphosphinyl)methyl-[1.1′-biphenyl]-3-yl)propanoic acid ethyl ester and (−)-di-O,O′-p-toluyl-L-tartaric acid as starting material, the title compound is obtained. The hydrochloride has a m.p. of 150°-152° (decomp.), $[\alpha]_D^{20} = -17.3°$ (c=1 in 2N HCl).

EXAMPLE 18

(−)-α-Amino-3-(5-phosphonomethyl-[1.1′-biphenyl]-3-yl)-propanoic acid ethyl ester In manner analogous to that described in Example 6 and using the compound of Example 17 as starting material, the title compound is obtained m.p. 277°-282° (decomp.) $[\alpha]_D^{20} = -4.4°$ (c=1 in 1N HCl), $[\alpha]_{365}^{20} = -28.1°$ (c=1 in 1N HCl).

EXAMPLE 19

(−)-α-Amino-3-(5-phosphonomethyl-[1.1′-biphenyl]-3-yl)propanoic acid

In manner analogous to that described in Example 16 and using the compound of Example 18 as starting material, the title compound is obtained, m.p. 274°-276° (decomp.) $[\alpha]_D^{20} = 0.0 \pm 0.5°$ (c=1 in 6N HCl), $[\alpha]_{365}^{20} = -20.3°$ (c=1 in 6N HCl).

The compounds of the invention exhibit pharmacological activity and are, therefore, useful as pharmaceuticals. In particular, the compounds exhibit central nervous system activity as indicated in standard tests. For example, the compounds inhibit the locomotion in mice.

In this test groups of 3 male mice (18-24 g, OF-1, Sandoz Basle) receive 3.2, 10, 32, 100 and 320 mg i.p. of the test drug. 1 hour after drug administration the mice are observed individually and their locomotion compared with that of control mice concurrently treated with vehicle. The locomotion is judged to be either unaffected, definitely more or less than controls, strongly more or less than controls, or completely inhibited.

Furthermore the compounds of the invention exhibit anticonvulsant activity as indicated in standard tests. In a first test, the compounds inhibit the electroshock-induced convulsions in the mouse [c.f. E. Swinyard, J. Am. Pharm. Assoc. Scient. Ed. 38, 201 (1949) and J. Pharmacol. Exptl. Therap. 106, 319 (1952)]. In this test groups of 3 mice (18-26 g, OF-1, Sandoz Basle) receive the test substance in a dosage of 3.2-100 mg/kg i.p. After 60 minutes a 50 mA, 200 ms long shock is applied with corneal electrodes smeared with electrolyte jelly. This supra-threshold shock produces tonic extensor convulsions of all extremities. Inhibition of the hindlimb extension is taken as a protective action. After investigation of several dose-levels an $ED_{min}$ is estimated.

In a second test the compounds inhibit N-Methyl-D-aspartic acid (NMDA) induced convulsions in the mouse. In this test groups of 6 female mice (18-26 g, OF-1, Sandoz Basle) were pretreated with the test substance in a dosage of 0.1-100 mg/kg i.p. 30 minutes later they are challenged with 400 mg/kg s.c. NMDA in the neck region and observed for 30 minutes. The latencies for the appearance of the first signs of convulsions, for the first tonic convulsions and for the occurrence of death are noted. The significance of any differences is observed using the Mann-Whitney U-test [S. Siegel, Non-parametric Statistics, McGraw-Hill, New York 1956]. After investigation of several dose-levels the threshold dose is estimated. This dose represents the smallest dose at which there is a significant inhibition of convulsive symptoms.

As a result of their anti-convulsant activity the compounds of the invention are useful in the treatment of epilepsy. For this indication, the appropriate dosage will, of course, vary depending upon, for example, the compound of the invention employed, the host, the mode of administration and the nature and severity of the condition being treated. However, in general, satisfactory results in animals are indicated to be obtained at daily dosages from about 0.1 to about 100 mg/kg animal body weight. In larger mammals, for example humans, an indicated daily dosage is in the range from about 25 to about 800 mg, e.g. from about 25 to 600 mg of a compound of the invention conveniently administered, for example, in divided doses up to four times a day.

The compounds of the invention further interact with excitatory amino acid systems, in particular they are competitive antagonists of NMDA (N-Methyl-D-aspartic acid) receptors, as indicated by an inhibitory effect on NMDA-induced depolarizations of the isolated amphibian spinal cord. This may be shown in the test performed in conventional manner (see for example D. R. Curtis et al., J. Physiol. (London) 150, 656-682 (1961) and R. H. Evans et al., Br. J. Pharmac. 67, 591-603 (1979) as follows:

A hemisected proximal part of the spinal cord of a toad or frog lies in a recording chamber being perfused by a Ringer solution (111 mM NaCl, 2 mM KCl, 2 mM $CaCl_2$, 12 mM Glucose, Tris-buffer (pH 7.5, 10 mM). The dorsal root is pulled into the stimulating chambers, the ventral root into the recording chambers. A stimulator connected to the stimulating chambers is used. A DC high impedance preamplifier measures the DC potential between the ground lead sampling the main chamber and one of the recording chambers. The signal from the pre-amplifier is monitored on a CRO to display stimulated synaptic activity (dorsal root—ventral root potential, DR—VRP) or to a chart recorder to display slow changes in potential. A copy of the preamplifier signal is fed into an integrator that calculates the area under the curve.

The excitatory amino acid agonists are applied at increasing doses of from 1 μM to 1 mM to determine dose response curves (DRC). After each dose, usually applied for 30 s to 1 min, the drug is washed out until control values of the VRP are reached. To measure the effect of each dose, the following procedure is used: The area under the curve measured by the integrator is sampled continuously at 1 min interval; the values for the last 5 min before the drug application are added to the values of the first 5 min after the VRP-slope has returned to control values and averaged. This average represents the control VRP and is deducted from the averaged values of the first 5 min after drug application. The effect of increasing doses are then measured and the numbers fed into a computer which constructs a dose response curve (DRC). From such DRCs $EC_{50}$ values are then determined graphically.

Antagonists are tested in two stages. The first stage consists of applying the agonist 3-5 times at a constant concentration near the $EC_{75}$ and repeating the procedure in presence of the antagonist. After a washout period the agonist alone is retested 3-5 times in order to evaluate recovery. The values obtained in such experiments are again fed into the computer which plots bardiagrams, calculates the means of the control-, drug- and recovery groups and tests statistically the difference between control and drug group. If a test drug shows inhibition in the first stage, competitive antagonism is tested in the second stage. This is done by determining a four point DRC of the agonist in the linear range and then repeating the DRC in presence of the putative antagonist at a constant concentration. Recovery is tested by repeating the DRC after the washout of the test drug. A first indication of competitive antagonism is given by a parallel shift to the right of the DRC in presence of the antagonist, e.g. compounds of the present invention at a concentration from 100 nM/1 to about 300 μM/1, e.g. 1 to about 300 μM/1. In such cases $pA_2$ values are calculated according to the formula $$pA_2 = \log I + \log (A50/B50 - 1)$$

where I is the concentration of the antagonist, A50 is the $EC_{50}$ for the agonist in presence of the antagonist and B50 the $EC_{50}$ of the agonist alone before the application of the test drug. Competitive antagonism can be confirmed by repeating the experiment with a double dose of the test drugs, if approximately the same $pA_2$ results there is a reasonable certainty that the antagonist is competitive (O. Arunlakshana et al., Brit. J. Pharmacol. 19, 48-58 (1959); M. Wenke, Drug receptor interactions. In BACQ ZM (ed) Fundamentals of biochemical pharmacology, Pergamon Press, Oxford, 357-381 (1971).

The compounds of the invention are also selective as indicated in that quisqualate induced depolarizations are not significantly effected in the above test wherein NMDA is replaced by quisqualicacid.

As a result of their NMDA receptor antagonism the compounds are useful in inhibiting GH and LH secretion and therefore useful i) in the treatment of disorders having an etiology comprising or associated with excess GH-secretion e.g. in the treatment of diabetes mellitus and angiopathy as well as of acromegaly and ii) in the treatment of disorders having an etiology associated with or modulated by excess LH-secretion e.g. in the treatment of prostate hypertrophy or in the treatment of menopausal syndrome. For these indications, the appropriate dosage will, of course, vary depending upon, for example the compound of the invention employed, the host, the mode of administration and the nature and severity of the condition being treated. However, in general for both uses i) and ii) above satisfactory results in animals are indicated to be obtained with a daily dosage of from about 0.01 to about 100 mg/kg animal body weight. In larger mammals, for example humans, an indicated daily dosage is in the range from about 1 to about 800 mg, e.g. from about 1 to about 600 mg of a compound of the invention conveniently administered, for example, in divided doses up to four times a day.

As a result of their NMDA receptor antagonism the compounds of the invention are further useful in the treatment of anxiety, schizophrenia and depression or of CNS degenerative disorders, such as Huntington's, Alzheimer's or Parkinson's diseases. For these indications, the appropriate dosage will, of course, vary depending upon, for example, the compound of the invention employed, the host, the mode of administration and the nature and severity of the condition being treated.

However, in general, satisfactory results in animals are indicated to be obtained with a daily dosage of from about 0.5 to about 30 mg/kg animal body weight. In larger mammals, for example humans, an indicated daily dosage is in the range from about 25 to about 800 mg, e.g. from about 25 to about 600 mg of a compound of the invention conveniently administered, for example, in divided doses up to four times a day.

The compounds of the invention protect further against hypoxiainduced degeneration of rat hippocampal neurons in vitro at concentrations ranging from 1 μM to 3 mM [method of S. Rothman, J. Neurosci. 4, 1884-1891 (1984)]. The compounds are therefore useful in the treatment of cerebral hypoxic/ischaemic conditions, e.g. stroke. For this indication the appropriate dosage will, of course, vary depending upon, for example, the compound of the invention employed, the host, the mode of administration and the nature and severity of the condition being treated. However, in general, satisfactory results in animals are indicated to be obtained at a daily dosage of from about 0.2 to about 10 mg/kg animal body weight. In larger mammals, for example humans, an indicated daily dosage is in the range from about 10 to about 800 mg of a compound of the invention conveniently administered, for example, in divided doses up to four times a day.

Furthermore, the compounds of the invention inhibit plasma corticosterone rise, which is induced by social stress in mice. This can be shown in the following test:

One day before the experiment a group of 5 male mice (40-50 g, OF-1, Sandoz,Basle) were placed in a transparent makrolon cage Typ 3, which is cut in halves by a grid. The next day each mouse was given an oral dose of 0.3-30 mg/kg of a compound of the invention, Two hours later an isolated male mouse was introduced for 15 minutes into the empty half of the cage and two trained observers recorded the behaviour of the mice in terms of acts such as dig, push-dig and rattle. Blood plasma samples were then taken from the tested mice group and assayed for corticosterone concentrations using a modified method of Paerson-Murphy B. E., J. Clin. Endocrinology 27 (1967) 973-990. The procedure was repeated with a control group of 5 mice which was given only a solvent.

As a result of their ability to inhibit plasma-corticosterone rise the compounds of the invention are useful in the treatment of stress-related psychiatric disorders, e.g. where the treatment of social withdrawal, which is present in many psychiatric disorders, e.g. schizophrenia, depression, generalized anxiety or in affective disorders, e.g. adjustment disorders with social withdrawal or anxiety, and other stress-related illnesses is desired. For this indication the appropriate dosage will, of course, vary depending upon, for example, the compound of the invention employed, the host, the mode of administration and the nature and severity of the condition to be treated. However, in general, satisfactory results in animals are indicated to be obtained at a daily dosage of from about 0.3 to about 30 mg/kg animal body weight. In larger mammals, for example humans, an indicated daily dosage is in the range from about 1 to about 800 mg of a compound of the invention conveniently administered, for example, in divided doses up to four times a day.

In the electroshock-induced convulsion test the Example 1 compound has an $ED_{min}$ of <50 mg/kg i.p. As an NMDA receptor inhibitor the Example 1 compound has a pA$_2$ of 7.3 at 5 μM.

The compounds of the invention may be administered by any conventional route, in particular enterally, preferably orally e.g. in the form of tablets or capsules, or parenterally e.g. in form of injectable solutions or suspensions.

The compound of Example 16 is the preferred compound for the treatment of stress-related psychiatric disorders. It has, for example, been determined that this compound inhibits significantly the rise of plasma-corticosterone at a dosage of 0.3 to 3 mg/kg p.o. in the above mentioned test method. It is, therefore, indicated that for the treatment of stress-related psychiatric disorders the compound of Example 16 may be administered at daily dosages of from 1 to 500 mg p.o., e.g. 1 to 100 mg, to larger mammals, for example humans.

The compounds of the invention may be administered as such or as their pharmaceutically acceptable salts. Such salts exhibit the same order of activity as the compounds of the invention in free base or free acid form. The present invention also provides pharmaceutical compositions comprising a compound of the invention as such or in salt form in association with at least one pharmaceutical carrier or diluent. Such compositions may be manufactured in conventional manner. Unit dosage forms contain, for example, from about 1 to about 400 mg of a compound of the invention as such or in its pharmaceutically acceptable salt form.

We claim:

1. A method of treating stress-related psychiatric disorders comprising administering to a subject in need of such treatment a therapeutically effective amount of a compound of formula I:

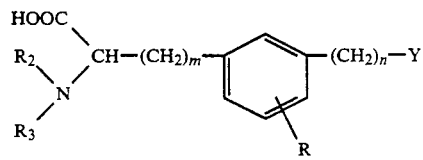

wherein
m and n are, independently, 1 or 2;
R$_2$ is hydrogen or (C$_{1-12}$)alkyl;
R$_3$ is hydrogen, (C$_{1-12}$)alkyl, (C$_{1-12}$)-alkylcarbonyl, (C$_{2-22}$)alkenylcarbonyl, (C$_{4-22}$)alkadienylcarbonyl, (C$_{6-22}$)alkatrienylcarbonyl, (C$_{8-22}$)alkatetraenylcarbonyl, (C$_{1-12}$)alkoxycarbonyl, or a group of formula II,

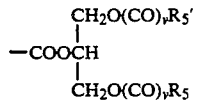

in which
R$_5$ and R$_5'$ are each, independently, (C$_{1-22}$)alkyl, (C$_{2-22}$)alkenyl, (C$_{4-22}$)alkadienyl, (C$_{6-22}$)alkatrienyl or (C$_{8-22}$)alkatetraenyl, and each v is, independently, 0 or 1;
R is unsubstituted phenyl or phenyl monosubstituted by halogen, (C$_{1-12}$)alkyl, (C$_{1-12}$)alkoxy or phenyl; and
Y is one of the groups a), b) or c)

 a)

 b)

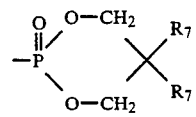 c)

where each R$_6$, independently, is (C$_{1-6}$)alkyl, and each R$_7$, independently, is hydrogen or (C$_{1-6}$)alkyl; or a pharmaceutically acceptable salt thereof.

2. A method according to claim 1 comprising administering to a subject in need of such treatment a therapeutically effective amount of (±)-α-amino-3-(5-phosphonomethyl-[1.1'-biphenyl]-3-yl)propanoic acid, or a pharmaceutically acceptable salt thereof.

3. A method according to claim 1 comprising administering to a subject in need of such treatment a therapeutically effective amount of (±)α-amino-3-(5-phosphonomethyl[1.1'-bi-phenyl]-3-yl)propanoic acid, or a pharmaceutically acceptable salt thereof.

* * * * *